United States Patent [19]

Webster et al.

[11] Patent Number: 4,810,438
[45] Date of Patent: Mar. 7, 1989

[54] METHOD OF CONTROLLING A RESIN CURING PROCESS

[75] Inventors: Charles N. Webster, Grand Prairie; Robert O. Scott, Bedford, both of Tex.

[73] Assignee: The United States of America as represented by the United States National Aeronautics and Space Administration, Washington, D.C.

[21] Appl. No.: 44,183

[22] Filed: Apr. 30, 1987

[51] Int. Cl.$^4$ .................. B29C 35/02; B29C 43/58; B29C 71/02; G06G 7/66

[52] U.S. Cl. .................. 264/40.6; 264/40.1; 264/40.5; 264/257; 264/347; 264/236; 264/DIG. 59; 364/473; 364/476

[58] Field of Search ............. 425/29, 30; 264/40.1, 264/40.5, 40.6, 257, 258, 297.5, 347, 345, DIG. 59, 236; 364/469, 473, 476, 557, 558

[56] References Cited

U.S. PATENT DOCUMENTS

| | | | |
|---|---|---|---|
| 3,049,410 | 8/1962 | Warfield et al. | 23/230 |
| 3,413,836 | 12/1968 | Nadeau et al. | 73/17 |
| 3,718,721 | 2/1973 | Gould et al. | 264/40 |
| 4,022,555 | 5/1977 | Smith | 425/30 |
| 4,140,050 | 1/1979 | Giddings | 100/38 |
| 4,312,212 | 1/1982 | Clendenin | 73/15.4 |
| 4,344,142 | 8/1982 | Diehr, II et al. | 425/30 |
| 4,371,483 | 2/1983 | Mattson | 264/40.6 |
| 4,382,052 | 5/1983 | Arimatsu | 425/29 |
| 4,455,268 | 6/1984 | Hinrichs et al. | 264/23 |
| 4,494,408 | 1/1985 | Delacy | 264/40.6 |
| 4,515,545 | 5/1985 | Hinrichs et al. | 425/143 |
| 4,517,146 | 5/1985 | Takasu | 264/40.6 |
| 4,542,466 | 9/1985 | Arimatsu | 264/40.6 |
| 4,551,807 | 11/1985 | Hsieh et al. | 364/473 |
| 4,589,072 | 5/1986 | Arimatsu | 264/40.6 |

Primary Examiner—James Lowe
Assistant Examiner—Jeremiah F. Durkin, II
Attorney, Agent, or Firm—Hardie R. Barr; John R. Manning; Edward K. Fein

[57] ABSTRACT

An analytical technique for controlling the curing process of fiber-reinforced composite materials that are formed using thermosetting resins. The technique is the percent gel method and involves development of a time-to-gel equation as a function of temperature. From this equation a rate-of-gel equation is then determined, and a percent gel is calculated which is the product of rate-of-gel times time. Percent gel accounting is used to control the proper pressure application point in an autoclave cure process to achieve desired properties in a production composite part.

12 Claims, 5 Drawing Sheets

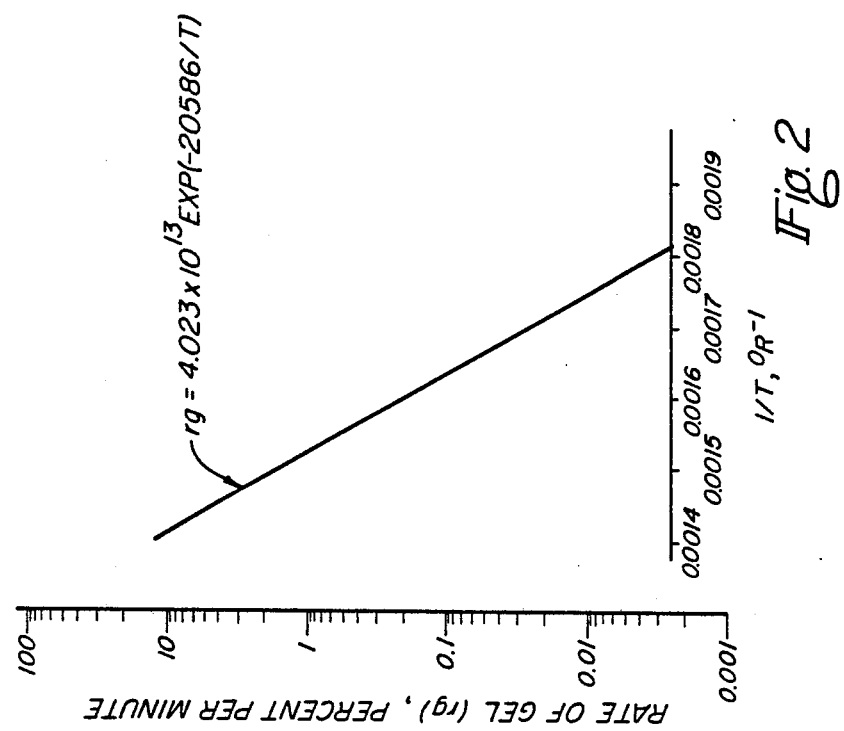
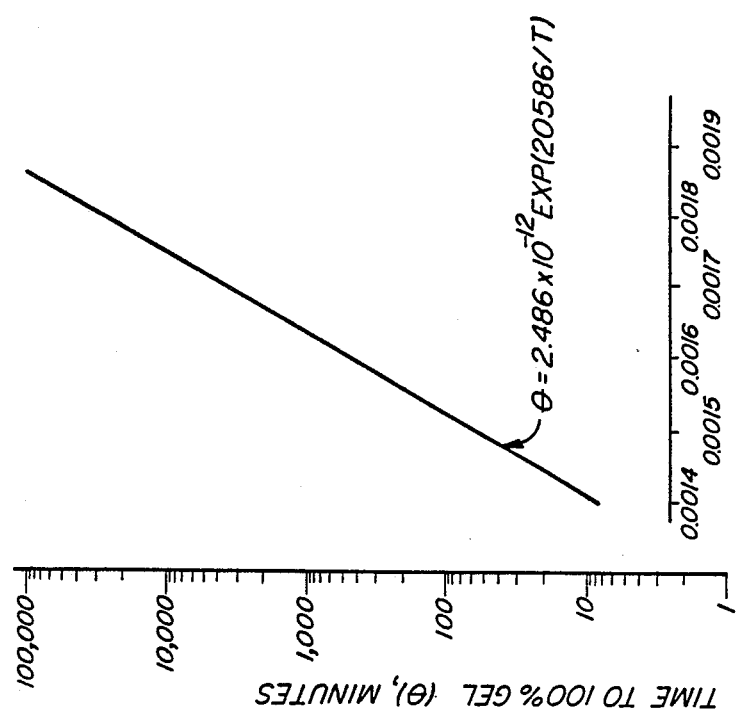

METHOD OF CONTROLLING A RESIN CURING PROCESS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The use of fiber-reinforced composite materials with thermosetting resins is increasing in the aerospace industry. Fibers such as glass, boron, graphite, and carbon are combined with resins such as epoxy, phenolic, polyimide and the like to achieve composites with high strength-to-weight ratios. The drawback of these composites is fabrication costs. Since the basic composite characteristics of strength, thickness, resin content and porosity are established at cure, finding an inexpensive cure control method, that would assure the desired property, has been a difficult task.

When a manufacturer receives a fabric that is impregnated with resin (prepreg), the resin is within an intermediate reaction state called the B-stage. The prepreg is pliable or will soften when warmed. With time and temperature the resin reaction will continue. Molecular weight increases due to polymer formation and cross linking as the resin advances through the B-stage state. At full advancement, the end of the B-stage reaction is reached when vitrification of the elastomeric structure occurs and the resin is no longer plastic when hot. Therefore, the layup and molding of production parts must be accomplished while the prepreg is still within the B-stage and is plastic when heated.

Cure of thermosetting resins is often done in an autoclave. One type of autoclave operating technique is to initially set the pressure at a low or moderate level. The part temperature is then increased, and the resin reaction advances within the B-stage state to a selected degree of polymer formation at which time the autoclave pressure is raised to create desired physical characteristics in the laminate. These characteristics are resin content, thickness, strength, and minimum microporosity. If the proper application of pressure in the autoclave is to produce a certain thickness or other physical property, for example, then that pressure must be applied when the resin has advanced to the proper amount of polymer formation but while it is still plastic and fusible. It is necessary therefore, to develop a method of monitoring and controlling the resin advancement within the B-stage while the resin is still plastic when hot.

As the resin advances in polymerization, the molecular weight increases. Viscosity also increases, and attempts have been made by other investigators to monitor viscosity change, by either dielectric changes or ultrasonic attenuation methods, to determine the pressure application point. But these methods are not without drawbacks, since viscosity is a function of temperature as well as advancement within the B-stage state. This means laminates at different temperatures that have the same viscosity reading could actually be at different states of advancement. Therefore, viscosity measurements would have to be correlated with thermal history to know the actual degree of advancement. This adds to the complexity of using viscosity measurements as an indication of resin advancement. Dielectric change measurements are also impractical when the reinforcing fibers are electrically conductive or when conductive fillers are added to the resin.

Autoclave operational techniques also have severe limitations since quite often a single autoclave cure cycle will be developed for use with all of the existing production parts. In this type of cycle, the temperature-time history and the pressure-time history, including the pressure application point, are preselected. Variation from laminate to laminate occurs in this type of cure even though the same amount of B-stage advancement is added in each autoclave run. This limitation is caused by the laminates coming to the autoclave at different degrees of advancement because of variations in their accumulated time-temperature histories, during the lay-up process.

These limitations indicate the need for a better technique to monitor resin advancement from the start of layup through cure so that consistent desired properties may be achieved.

2. Background art

A review of the prior art reveals the following U.S. patents which relate to technology more or less pertinent to some aspects of the present invention.

U.S. Pat. No. 3,718,721 to Gould, et al. discloses a method for controlling the state of cure in a mold which involves the monitoring of the temperature as a function of time. The state of cure of a predetermined site in the article is computed from the temperature measurements.

U.S. Pat. No. 3,049,410 to Warfield, et al. shows a method of determining the optimum temperatures for bulk curing of resins. It involves determining minimum curing time and determining the effect of temperature on the rate of cure using measurement of changes in electrical resistivity of samples during polymerization.

U.S. Pat. No. 3,413,836 to Nadeau, et al. discloses an apparatus for detecting a change of state in a liquid sample, such as a gel point or freezing point, involving detection of changes in amplitude of oscillatory motion of a liquid sample and a reference fluid within two containers.

U.S. Pat. No. 4,312,212 to Clendenin shows an apparatus for measuring the length of time necessary to heat an epoxy resin prepreg to a tacky condition.

None of the prior art including the above patents relate however specifically to a percent gel parameter for controlling an autoclave nor do they relate to a process which includes such features as (1) determining the initial state of cure of a sample, together with (2) determining the amount of total energy (time and temperature) required to complete gellation, (3) accounting for the resin cure advancement at all stages of processing so that (4) final processing steps (typically autoclave) may be adjusted to achieve pressure application at the optimum point in the processing cycle prior to 100% gellation. None of the prior art teaches a method sensitive enough to achieve uniform product results despite differences in the layup history of various batches.

SUMMARY OF THE INVENTION

This invention relates to a process control technique used as an analytical tool for controlling the curing process of fiber-reinforced composite materials formed using thermosetting resins. The technique has been used during the development of advanced carbon-carbon (ACC) material for the Space Shuttle Orbiter's Leading Edge Structural Subsystem (LESS). The process control method is based upon percent gel. Percent gel measures the advancement state of the resin, and the calculation is related to the resin reaction rate. Achieving a desired physical characteristic in a composite is based on percent gel as a parameter during layup and cure to control the time pressure increase during cure.

The need for more control of composite cure processes has been noted, and even though the same autoclave cure cycle is used, the resulting laminates may have different properties. In the cure of large complex shapes, differences are found within a single production part. The objective has been to find a controlling parameter that produces a uniform production part and assures uniformity from one cured production part to the next. Accounting for percent gel has been found to be an analytical tool useful to control the curing process.

The percent gel technique provides an analytical method to monitor the accumulated advancement of a thermosetting resin. Not only does it provide a useful method during autoclave cure, but it also provides a mechanism to calculate resin advancement during layup. By virtue of the present invention the degree of pre-autoclave resin advancement can now be determined. The autoclave cure cycle hold time can be adjusted to bring the production part to the selected percent gel point for autoclave pressure increase. This assures consistent laminates from run to run regardless of the differences in pre-autoclave histories. Knowing the preautoclave percent gel, the only measurement required to perform this is laminate temperature variation with elapsed time. Therefore, this technique is convenient to initiate since it uses existing measurements. Although the percent gel method is well suited for use with a computer-controlled autoclave, such control is not a requirement. It is equally useful for other autoclaves since the required calculations can be done manually. Percent gel, therefore, is an analytical tool which sums the resin advancement from its as received condition until it is no longer "plastic when hot" and can be used to assure consistent laminates from one autoclave run to the next.

The invention also relates to a process control technique for controlling the curing process of fiber-reinforced composite materials formed using thermosetting resins. The technique involves determining by test the amount of energy (time at temperature) required for 100% gellation of a particular prepreg material, accounting for the accumulated time-temperature energy which a laminate is subjected to during its history, and controlling the rate of further time-temperature energy additions in concert with additional processing steps, in order to increase autoclave pressure at the optimum point in the manufacturing process prior to 100% gelation.

In a more specific embodiment of the invention, there is featured a method of monitoring and controlling the curing process in an autoclave of fiber-reinforced thermosetting resin composite materials in order to establish at cure predetermined composite characteristics of strength, thickness, resin content and porosity, in a production part comprising the steps of developing a time-to-gel equation as a function of temperature for the resin to be subjected to a cure cycle in the autoclave, determining a rate-of-gel equation from the time-to-gel equation in the previous step, calculating a percent gel as a controlling parameter for the cure cycle of the autoclave from the rate-of-gel equation, selecting a series of desired properties of the resin to be subjected to the cure cycle of the autoclave as a function of the percent gel so calculated, and controlling the operation of the autoclave cure cycle system in accordance with the percent gel parameter in order to achieve the selected desired resin properties.

Another feature of the present invention includes the autoclave control system which is fully automated and has input parameters of accumulated percent gel prior to the autoclave run, the desired percent gel when the autoclave pressure is raised, the time-temperature profile and the autoclave pressure profile, and the process further includes the steps of measuring the autoclave pressure, air temperature, and the temperature of the production part during the autoclave cycle, providing elapsed time for calculating the percent gel and for loop control logic calculations, employing the percent gel calculations in the pressure control logic and in the temperature control logic of the control system, and employing the production part temperature control logic to signal completion of the heating phase and the completion of the autoclave cycle.

Other advantages of this invention will be apparent from the descriptions which follow in conjunction with the accompanying drawings and claims.

BRIEF DESCRIPTION OF THE DRAWINGS

FIG. 1 is a graph showing the time-to-gel relationship for graphite fabric impregnated with HEXCEL R120 phenolic resin.

FIG. 2 is a graph illustrating the rate-of-gel relationship for graphite fabric impregnated with HEXCEL R120 phenolic resin.

DETAILED DESCRIPTION OF THE PREFERRED EMBODIMENT

Figure 3:
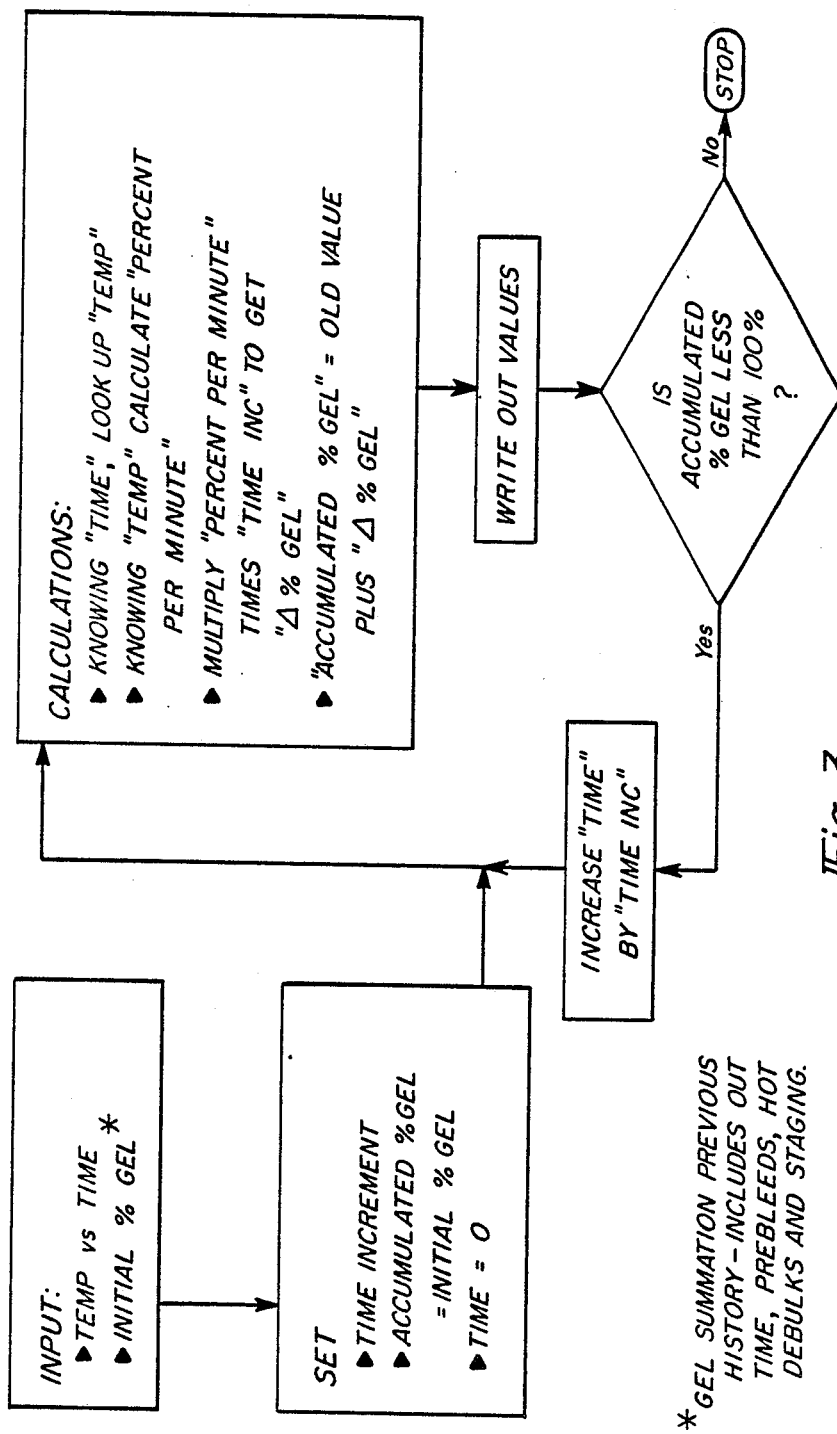
FIG. 3 is a flow chart in the form of a functional representation of a calculation procedure for percent gel.

Layup and molding of composite shapes is done while the prepreg is in the B-stage state where the resin softens and is plastic while hot. The end of the "plastic while hot" phase is defined to be 100% gel. The time required for the resin to advance from the as received condition to the 100% gel condition depends on the resin temperature history. The higher the temperature the shorter the time to 100% gelation. One method is to determine the time required to reach 100% gel is the flow or no-flow test. Small prepreg samples are staged at constant temperature for varying lengths of time. As a sample is removed from staging, it is quickly pressed to check for resin squeeze out beyond the boundary of the fabric. When no resin is squeezed out, the 100% gel point has been reached. An alternative method to determine the time-to-gel is the constant temperature Rheology test.

By obtaining time-to-gel data at several temperatures, sufficient data is gathered so that a time-to-gel equation is developed as a function of temperature. The procedure is to plot the time-to-gel data on semi-logarithmic graph paper in the Arrhenius form shown in FIG. 1. The abscissa is the reciprocal of the absolute temperature where temperature is expressed in °R or °K. The ordinate is the time-to-gel on a logarithmic scale. For each data point, the time-to-gel is plotted at the reciprocal of the test temperature. Plotted in this form, the time-to-gel data are found to behave like a single, temperature-dependent reaction. A straight line is then drawn through the data points. Using standard analytic geometry techniques, such as the point-slope method, an equation may be written for the line. The equation may then be reduced to a convenient form. For example, tests on PAN based, heat stabilized, graphite fabric impregnated with HEXCEL R120 phenolic resin indicate the time-to-gel to be 3.5 to 3.75 hours at 180° F. These and additional data have been plotted in the Arrhenius form, and the time-to-gel equation has been determined to be:

$$\theta = 2.486 \times 10^{-12} \, EXP \, (20586/T)$$

where $\theta$ is the time-to-gel in minutes and T is the absolute temperature in °R. Values for the HEXCEL R120 material noted above are set forth in FIG. 1 and as follows:

| Temperature, °F. | Time-to-gel |
|---|---|
| 40 | 3.6 years |
| 70 | 128 days |
| 175 | 298 minutes |
| 250 | 10 minutes |

Determining the rate-of-gel follows from knowing the time-to-gel. For example, at a given temperature, the time-to-gel equation predicts 100% gel in $\theta$ minutes. Therefore, at that temperature, the rate-of-gel (percent per minute) is 100% divided by $\theta$ minutes. The rate-of-gel ($r_g$) equation can thus be written in the Arrhenius form:

$$r_g = K \, EXP \, (-E/RT)$$

where:
$r_g$ = rate-of-gel, % per minute
K = specific reactivity, % per minute
E = Activation energy, BTU/lb-mole
R = gas constant, BTU/lb-mole-R°
T = Temperature, °R
For the HEXCEL R120 example above:

$$K = 4.023 \times 10^{13},$$

E/R = 20586, and
$r_g = 4.023 \times 10^{13} \, EXP \, (-20586/T)$ % per minute.

The rate-of-gel for the HEXCEL R120 is presented in FIG. 2.

Percent gel is therefore the product of rate-of-gel times the time. When the temperature-time history of the prepreg is known and the rate-of-gel equation is known, these values can be combined to give rate-of-gel versus time. The area under such curve is the percent gel. This method lends itself to calculator or computer methods to sum the incremental amounts of percent gel with time to track the accumulated percent gel.

The rate-of-gel equation for the HEXCEL R120 resin shows the rate of advancement to double with every 10° F. rise in temperature. It becomes necessary then to account for all the time-at-temperature to which the material is exposed from the time it is received to the point of 100% gel. When the prepreg is under refrigeration, the advancement rate is sufficiently low that it is negligible. The following is a list of situations for which an accounting for percent gel is necessary:

A. out time at room temperature,
B. elevated temperature pre-bleed operations, if any,
C. hot debulk steps, if any,
D. staging temperature history, if any,
E. autoclave temperature-time profile.

The amount of advancement (% gel) accumulated in these various operations has been found to be additive. That is, the percent gel due to out time may be calculated separately and then added to the percent gel due to prebleeds, etc. Accounting for these layup events shows that various laminates arrive at the autoclave at different degrees of advancement. For this reason, a set autoclave cycle will not result in consistent production parts.

If the autoclave pressure is to be raised when the laminate is at a certain degree of advancement, adjustments must be made based on the pre-autoclave history of the laminate.

Percent gel calculations for an autoclave run can be made using the flow chart of FIG. 3. Input requirements are: the temperature-time history and the percent gel that has been accumulated prior to the autoclave run. The program would set: (1) the "time increment", (2) "time" equal to zero, and (3) the "accumulated percent gel" equal to the initial percent gel. Calculations begin by finding the temperature at the current time. Based on temperature, the rate-of-advancement is then calculated. The increment of percent gel is calculated by multiplying the rate-of-gel times the time increment. This amount of gel is added to the previous total to arrive at the current value. If the accumulated percent gel is less than 100%, the elapsed time is increased by the time increment and the calculations must continue. When the accumulated percent gel reaches 100%, the calculations stop.

Figure 5:
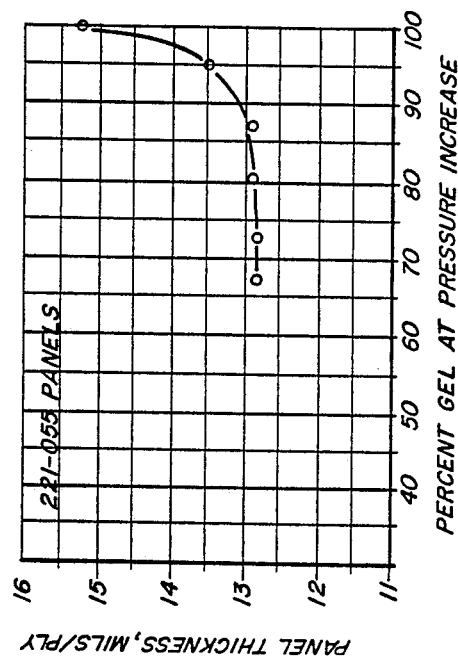
FIGS. 5–7 are graphs similar to FIG. 4 but showing the variation in some of the properties of the panels with percent gel. The properties shown are ply thickness, porosity, and flexure strength.
Figure 4:
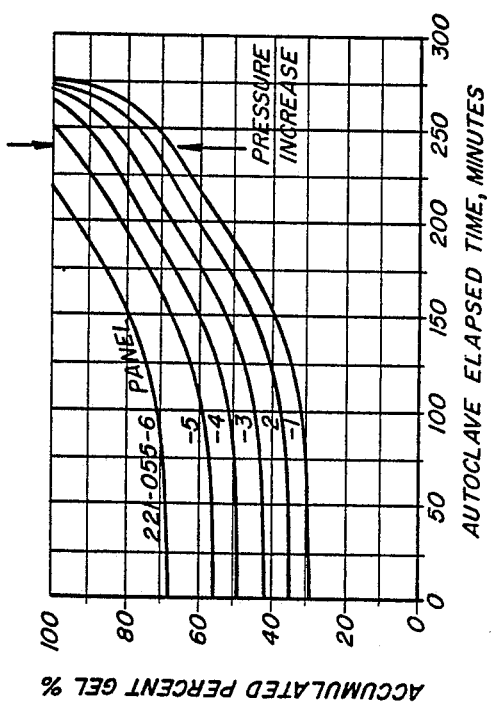
FIG. 4 is a graph showing the percent gel analysis of an autoclave run on six flat panels fabricated with HEXCEL R120/ACC prepreg.
Figure 7:
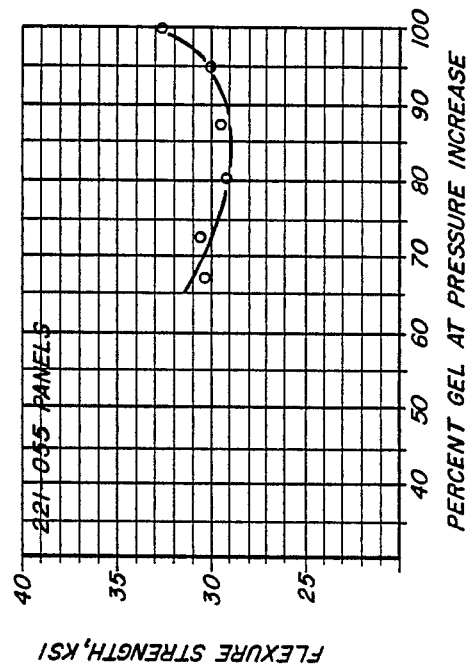
Figure 6:
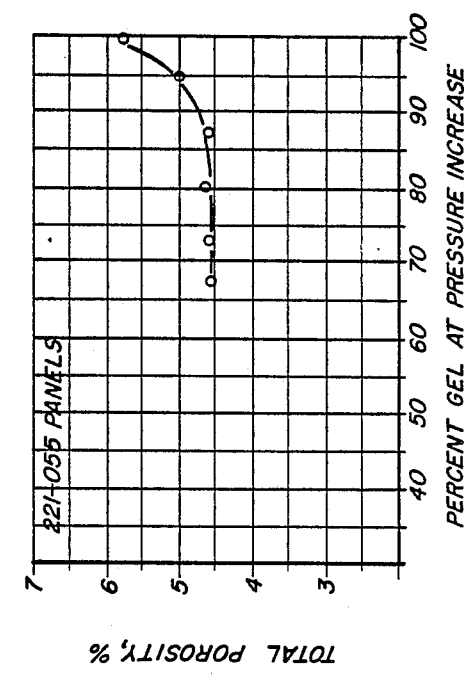

Percent gel is used to determine the pressure application point to optimize properties for a given application. For example, six flat panels were fabricated using the HEXCEL R120/ACC prepreg previously mentioned. The panels were staged to different amounts of percent gel prior to the autoclave run. All six panels were cured on the same platen. The percent gel analysis of the autoclave run is shown in FIG. 4. The initial variation in percent gel was created by differential staging during layup. Because of this, the panels ranged from 67% gel to 100% gel when the autoclave pressure was raised. Thus the pre-autoclave history of a laminate has an influence on the cured production part. The resulting variations in some of the properties are shown in FIGS. 5–7. FIG. 5 shows the per ply thickness variation with percent gel at pressure application. This data is used to determine when to apply pressure to achieve a given thickness of laminate. The total porosity variation with percent gel is given in FIG. 6, and is relatively flat from 67% gel to 87% gel and then exhibits a significant increase. There is some scatter in the flexure strength values of FIG. 7 which indicate a minimum value when the pressure is increased at 80-90% gel.

To achieve a desired property in a production part, test panels similar to those noted are built using the composite materials. The variation in properties with percent gel is determined (similar to FIGS. 5-7). The amount of percent gel at pressure application is then determined to produce the desired result. Producing the desired result in a production part is then a matter of accounting for the accumulated percent gel. Calculating the pre-autoclave advancement due to out time, hot debulks, staging and the like yields the accumulated percent gel at the start of the autoclave cure. When this initial value is subtracted from the desired percent gel at pressure application, the amount of percent gel to be added in the autoclave is determined. The proper amount of advancement in the autoclave is added by varying the length of a constant temperature hold step so that the proper amount of advancement is achieved before the autoclave pressure is increased.

From the above, it should be apparent that percent gel is a useful method of tracking thermosetting resin advancement from the time the resin is received until it is no longer plastic when hot. The only measurement needed in order to track the accumulated advancement (percent gel) is the resin (laminate) temperature versus time. Laminate physical properties have also been shown to be a function of percent gel when the autoclave pressure is raised. Thus a desired physical property is therefore achieved by use of percent gel to determine the pressure application point. Hence by tracking the accumulated percent gel during layup and cure, the pressure application point is duplicated from production part to production part even when the production parts arrive at the autoclave at different states of advancement.

Operation

The percent gel technique is useful in the cure of any thermosetting resin whose B-stage advancement is a function of time and temperature. Once the time-to-gel has been determined as a function of temperature, the procedure can be carried out with available time and temperature measurements. Better control of resin cure is thereby provided since all of the advancement is monitored with set autoclave cure cycles producing varied results, and hence the pre-autoclave advancement is the tool to render cure cycle adjustments which assure consistent results.

"Percent gel" is therefore a process control parameter applicable to autoclave control in several ways. The first is to perform manual calculations during the autoclave run by reading production part temperatures from the chart recorder and making real-time calculations using a calculator or computer not connected to the autoclave operation. These calculations follow the calculation procedure of FIG. 3 and are used to determine the pressure application point in the autoclave run.

A second procedure is to preselect the time at which to raise the autoclave pressure. This approach is used, for example, when a given autoclave temperature-time profile is used to build production parts. In this case, the production part temperature transient and temperature during a constant temperature hold period are repeatable from run to run. Since the temperature is known with respect to autoclave time, the percent gel with autoclave time is determined using the procedure of FIG. 3. The result is the accumulated percent gel that is added in the autoclave as a function of autoclave time. The amount of percent gel accumulated in layup is then subtracted from the percent gel desired at pressure application to determine the percent gel to be added in the autoclave prior to the pressure application. The elapsed time in the autoclave prior to the pressure application point is then selected.

Figure 8:
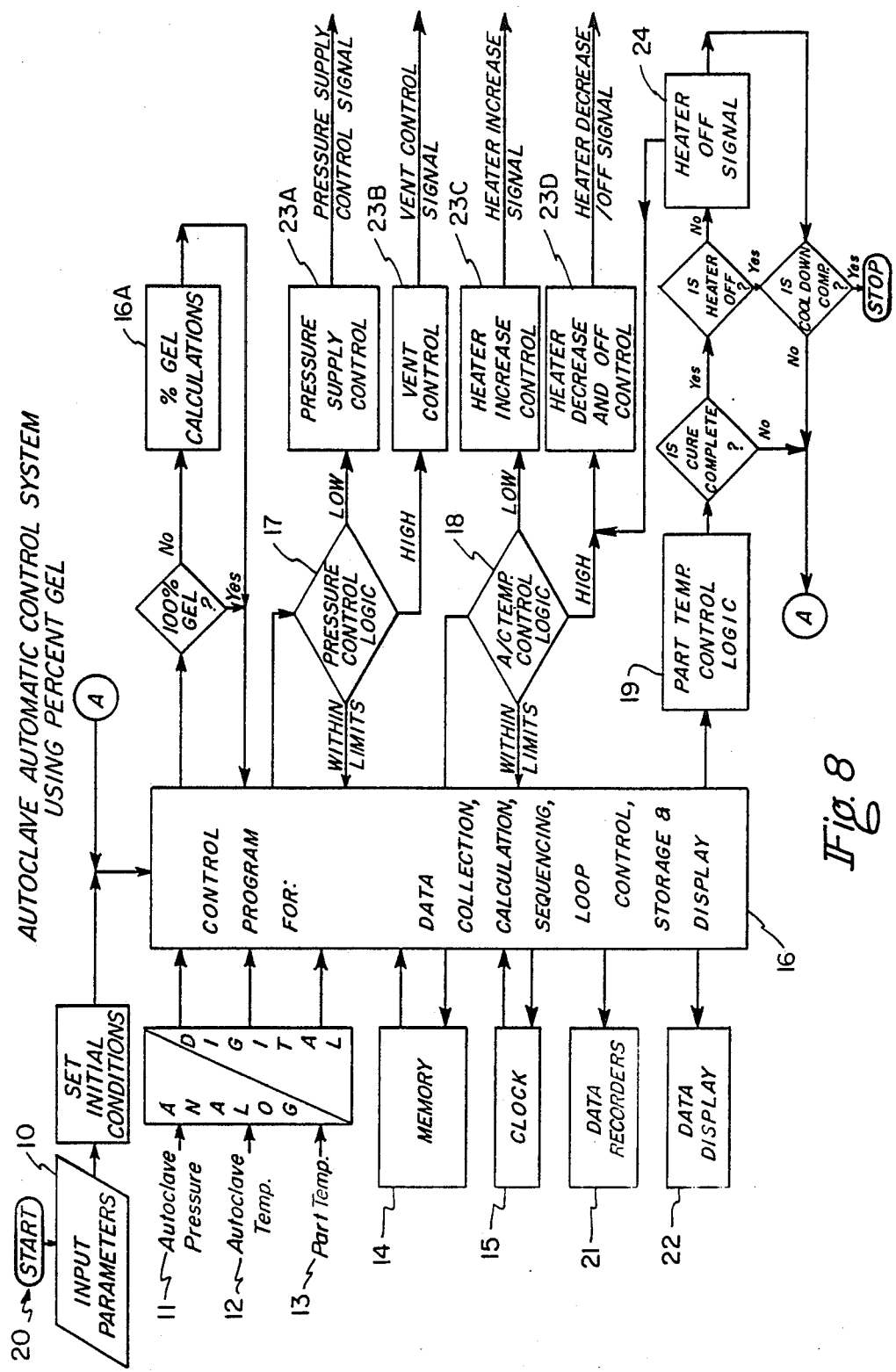
FIG. 8 is a functional representation of a typical autoclave automatic control system using percent gel in accordance with the principals and precepts of the present invention.

Percent gel may also be used as the process control parameter of a fully automated autoclave control system 20 similar to that shown in FIG. 8. The input parameters 10 would include the accumulated percent gel prior to the autoclave run and also the desired percent gel when the autoclave pressure is raised. Additional input parameters would be the time-temperature profile and the autoclave pressure profile. Using this technique, only autoclave pressure 11, autoclave temperature 12, and production part temperature 13 are required to be measured during the run. Memory 14 is required for storing values to check against control limits. A clock 15 provides elapsed time for the percent gel calculations and loop control logic 16. The percent gel calculations 16A are used in the pressure control logic 17 and also the temperature control logic 18. The production part temperature control logic 19 signals the completion of the heating phase and the completion of the autoclave run.

The system of FIG. 8 also includes the standard type data recorders 21 and data display equipment 22, as well as control features 23A-D for transmitting signals to the autoclave. A heater signal control 24 also feeds control feature 23D in order to adjust the operation of the autoclave heater in response to the production part temperature control logic 19.

While a single embodiment of the invention has been described, variations thereof can be made without departing from the teachings of the invention. Therefore it is intended that the scope of the invention be limited only by the claims which follow.

I claim:

1. The method of monitoring and controlling the curing process of fiber-reinforced thermosetting resin composite materials in order to establish after cure, predetermined composite characteristics of strength, thickness, resin content and a porosity, which are uniform from one article to the next despite variations in the percent gel, or state of gelation, of the different articles, due to their different histories of temperature and time-at-temperature prior to a heating phase comprising the steps of;
  (a) determining the percent gel already existing in a particular batch of composite material at some point in time;
  (b) accumulating and accounting for additional percent gel due to the temperature and time-at-temperature of all intervening steps, including a fabrication steps, said intervening steps being those subsequent to determination of the initial percent gel and prior to the heating phase;
  (c) calculating, on the basis of steps (a) and (b) and the desired product characteristics, the percent gel remaining to be accomplished prior to a pressure increasing step which is to be conducted, at least in part, simultaneously with the heating phase;
  (d) initiating the heating phase;
  (e) controlling the temperature and time-at-temperature during the heating phase to accomplish the desired percent gel prior to initiation of the pressure increasing step;

(f) initiating the pressure increasing step at the desired percent gel;

(g) controlling the temperature and time-at-temperature during the remainder of the heating phase to accomplish 100% percent gel, complete gelation.

2. The method of claim 1 wherein the fiber is selected from the group consisting of glass, boron, graphite and carbon.

3. The method of claim 2 wherein the resin is selected from the group consisting of epoxy, phenolic, and polyimide.

4. The method of claim 2 wherein the resin is selected from the group consisting of thermosetting resins whose B-stage advancement rate can be characterized in the form:

$$r_g = K \, EXP \, (-E/RT)$$

where:
$r_g$ = Rate-of-gel, % per minute
K = Specific Reactivity, % per minute
E = Activation Energy, BTU/lb-mole
R = Gas Constant, BTU/lb-mole-R
T = Temperature, °R 5. The method of claim 3 wherein the pressure increasing step and the heating phase are conducted while the resin is within the B-stage intermediate reaction state where the resin softens and is plastic while hot.

6. The method of claim 1 where the percent gel remaining to be accomplished is determined by use of a time-to-gel equation in the form:

$$0 = 2.486 \times 10^{-12} \, EXP \, (20586/T)$$

where 0 is the time-to-gel in minutes and T is the absolute temperature in °R.

7. The method of claim 6 wherein the material is graphite fabric impregnated with a phenolic resin.

8. The method of claim 7 wherein the time-to-gel for the resin is as follows:

| Temperature °F. | Time-To-Gel |
| --- | --- |
| 40 | 3.6 Years |
| 70 | 128 Days |
| 175 | 298 Minutes |
| 250 | 10 Minutes |

9. The method of claim 6 where the time-to-gel equation is developed by preparing a series of samples of the resin impregnated fabric and heating them at a constant temperature for varying lengths of time, and pressing each sample in order to establish resin squeeze-out beyond the boundary of the fabric.

10. The method of claim 6 where the time-to-gel equation is developed by preparing a series of samples of the resin impregnated fabric and measuring time-to-gel using constant-temperature Rheology methods.

11. The method of claim 1 wherein the pressure increasing step and the heating phase are performed within an autoclave having temperature and time control such that the autoclave control allows for differing stages of pre-autoclave advancement of the resin composite under cure by subtracting the amount of percent gel accumulated prior to the heating phase from the percent gel desired at initiation of pressure increasing step in order to determine the percent gel to be added in by the autoclave prior to the pressure increasing step, and the percent gel to be added in by the autoclave during the remainder of the heating phase.

12. The method of claim 1 wherein the pressure increasing step and the heating phase are performed within an autoclave having an autoclave control system and wherein the autoclave control system is fully automated and includes input parameters of accumulated percent gel prior to the autoclave run, the desired percent gel when the autoclave pressure is raised, the time-temperature profile and the autoclave pressure profile, and the process further includes the steps of measuring the autoclave pressure, autoclave temperature, and the temperature of the production part during the autoclave cycle, providing elasped time for calculating the percent gel and for loop control logic calculations, employing the percent gel calculations in the pressure control logic and in the temperature control logic of the control system, and employing the production part temperature control logic to signal completion of the heating phase and the completion of the autoclave cycle.

* * * * *